United States Patent [19]

Boitiaux et al.

[11] Patent Number: 4,724,274

[45] Date of Patent: Feb. 9, 1988

[54] PROCESS FOR PRODUCING 2-METHYL-2-BUTENE FROM A 5 CARBON ATOM OLEFINS CUT CONTAINING 2-METHYL-1-BUTENE AND AT LEAST ONE N-PENTENE

[75] Inventors: Jean-Paul Boitiaux, Poissy; Jean Cosyns, Maule; Michel Derrien, Rueil-Malmaison, all of France

[73] Assignee: Institut Francais Du Petrole, Rueil-Malmaison, France

[21] Appl. No.: 826,157

[22] Filed: Feb. 4, 1986

[30] Foreign Application Priority Data

Feb. 4, 1985 [FR] France ............................. 85 01612

[51] Int. Cl.$^4$ ............................................. C07C 5/23
[52] U.S. Cl. ...................................... 585/668; 585/670
[58] Field of Search ............................... 585/668, 670

[56] References Cited

U.S. PATENT DOCUMENTS

| | | |
|---|---|---|
| 3,531,545 | 9/1970 | Garner et al. . |
| 3,772,400 | 11/1973 | Garner et al. ...................... 585/670 |
| 4,132,745 | 1/1979 | Amiques et al. .................... 585/668 |

FOREIGN PATENT DOCUMENTS 47-48362  6/1972  Japan .................................. 585/668

*Primary Examiner*—Curtis R. Davis
*Attorney, Agent, or Firm*—Millen & White

[57] ABSTRACT

Process for producing 2-methyl-2-butene from a charge containing olefins of 5 carbon atoms, including 2-methyl-1-butene and at least one n-pentene, wherein a mixture of said charge with hydrogen and at least one sulfur compound is contacted with a supported catalyst comprising at least one noble metal from group VIII.

The 2-methyl-1-butene of the charge is isomerized to 2-methyl-2-butene and the n-pentenes are hydrogenated.

13 Claims, No Drawings

PROCESS FOR PRODUCING 2-METHYL-2-BUTENE FROM A 5 CARBON ATOM OLEFINS CUT CONTAINING 2-METHYL-1-BUTENE AND AT LEAST ONE N-PENTENE

BACKGROUND OF THE INVENTION

Cracking processes such as steam-cracking, visbreaking, coking, catalytic cracking, provide $C_5$ cuts of high olefin content. Some of them may contain substantial amounts of methyl-butenes (isopentenes). In particular, catalytic cracking $C_5$ cuts may contain up to 30% of a mixture of 2-methyl-1-butene, 2-methyl-2-butene and 3-methyl-1-butene. An example of composition of such a cut is given in the following table:

TABLE 1

| HYDROCARBON | % BY WEIGHT | BOILING POINT °C. |
|---|---|---|
| Isopentane | 38.8 | |
| n-pentane | 14.2 | |
| Cyclopentane | 2.1 | |
| 1-pentene | 1.9 | 29.20 |
| cis-2-pentene | 6.0 | 37.80 |
| trans-2-pentene | 8.7 | 36.25 |
| 2-methyl-1-butene | 9.5 | 38.60 |
| 2-methyl-2-butene | 17.5 | 38.40 |
| 3-methyl-1-butene | 1.0 | 20.00 |
| Isoprene | 0.3 | |

This table indicates the boiling points of the various olefins of the cut. It can be seen that the latter are very close to each other so that, in particular, it is impossible to separate methyl-butenes from 2-pentenes by fractional distillation.

The invention has as an object the provision of a process for the conversion of 2-methyl-1-butene continued in a $C_5$ olefins cut, optionally containing paraffins, to 2-methyl-2-butenes. Said conversion is without substantial hydrogenation of said methyl-butenes but with substantial hydrogenation, preferably almost complete hydrogenation, of n-pentenes.

When the charge further contains a $C_5$ diolefin, the invention has as an object the hydrogenation of said diolefin.

2-methyl-2-butene is an important raw material for many syntheses, for example for producing alcohols or ethers or producing isoprene by dehydrogenation. In these applications, the presence of $C_5$ saturated hydrocarbons is usually not inconvenient.

In order to obtain 2-methyl-2-butene with a good degree of purity, it was necessary, up to now, to employ sulfuric acid extraction, providing an iso-pentenes mixture of 95-97% purity. During the extraction, the double bond shifts so that the final mixture contains approximately 90% of 2-methyl-2-butene and 10% of 2-methyl-1-butene. The process using sulfuric acid suffers however from many disadvantages. The first one is its high cost, mainly as a result of the sulfuric acid consumption. As a matter of fact, the presence in the charge of such diolefins as isoprene results in an overconsumption of sulfuric acid due to the formation of acid muds whose removal is always difficult and costly. A second disadvantage results from the fact that the obtained isopentene cut is not completely pure and still contains a small amount of linear olefins.

SUMMARY OF THE INVENTION

A new process has now been found, whereby it is possible, from a mixture of pentenes and isopentenes, to obtain a cut which practically contains only isopentenes as olefins. In said cut, the major part of isopentenes consists of 2-methyl-2-butene, the other hydrocarbons thereof being mainly n-pentane and isopentane. Thus, isopentenes are obtained with a purity degree of almost 100% with respect to the other olefins. The other hydrocarbons, being paraffinic, may be considered as inert solvents and usually do not disturb subsequent processes for converting 2-methyl-2-butene.

The new process consists of contacting hydrogen and a charge containing olefins of 5 carbon atoms, including 2-methyl-1-butene and at least one n-pentene, with a supported catalyst containing at least one noble metal from group VIII, at a temperature of 20° to 150° C., for example from 50° to 150° C. and preferably from 60° to 120° C. According to an essential feature of the process, the reactants mixture contains 2 to 50 ppm by weight of at least one sulfur compound, expressed as sulfur, with respect to the hydrocarbon charge, and the pressure is 5-100 bars, for example from 20 to 100 bars and preferably 25-50 bars.

It is apparent that the process essentially concerns hydrocarbon charges whose respective contents of 2-methyl-2-butene and 2-methyl-1-butene respectively correspond to a content of 2-methyl-2-butene lower than the proportion of thermodynamic equilibrium; it also concerns charges containing 2-methyl-1-butene without any 2-methyl-2-butene.

The new process comprises a selective hydrogenation of linear olefins to the corresponding paraffins accompanied with an isomerization of 2-methyl-1-butene to 2methyl-2-butene. A supported catalyst is used which comprises at least one noble metal from group VIII. Palladium is preferred for its higher selectivity. Any one of the usual carriers may be used, for example alumina, silica or carbon. A preferred catalyst comprises 0.01 to 2% (preferably 0.1 to 0.5%) by weight of palladium on a carrier, preferably on alumina.

The catalyst may be used as a moving bed, but a fixed bed is preferred. The operating conditions of this new process are so selected as to achieve not only the isomerization of 2-butyl-1-butene to 2-methyl-2-butene, but also an extensive hydrogenation of n-pentenes while avoiding a substantial hydrogenation of the desired methyl-butenes.

The $C_5$ cut feed rate may range from 0.5 to 20, preferably from 1 10 liters (in liquid state) per liter of catalyst and per hour. The hydrogen flow rate is so selected as to extensively hydrogenate n-pentenes without substantially hydrogenating isopentenes. The hydrogen amount, in number of moles, will be at least equal to the number of moles of n-pentenes in the charge and will be more generally in the range from 5 to 90 moles percent with respect to the $C_5$ hydrocarbons of the feed.

The judicious selection of these conditions is however not sufficient, in the absence of sulfur compound, for hydrogenating pentenes as selectively as desirable. It is hence necessary to proceed in the presence of at least one sulfur compound, in an amount from 2 to 50 ppm by weight, preferably 5-30 ppm by weight, expressed as sulfur, with respect to the hydrocarbons charge. The sulfur compound may be a normal component of the charge to be treated or may be added thereto when necessary.

The sulfur may be present as an inorganic or organic compound, for example as hydrogen sulfide, thiol, sulfide, disulfide, thiophene, thiourea, thioaldehyde, thioketone, dithiocarbamate, thiocyanate or any other compound optionally comprising such substituents as hydroxy, amino, carboxy, halide or similar groups. Examples are dimethylsulfide, dimethyldisulfide, ethanethiol, thioacetone, butanethiol and carbon sulfide.

In the absence of sulfur compounds in the charge it is not possible to selectively remove linear pentenes; a substantial part of the isopentenes is hydrogenated to the corresponding paraffins, thereby decreasing the yield to 2-methyl-2-butene.

EXAMPLES

The following non limitative examples illustrate the invention.

EXAMPLE 1

(comparison)

In this example the treated hydrocarbons charge has the following composition:

|  | % by weight |
| --- | --- |
| 1-pentene | 25 |
| 2-methyl-1-butene | 40 |
| Pentane | 35 |

The sulfur concentration of the charge is lower than 1 ppm by weight.

This charge is passed over a fixed bed of catalyst consisting of 0.3% by weight of palladium deposited on tetragonal gamma alumina shaped as balls and having a specific surface of 60 m2/g. The catalyst fixed bed is placed in a tubular reactor maintained in substantially isothermal conditions. Before use, the catalyst is reduced at atmospheric pressure in a hydrogen stream at 100° C. for 2 hours.

The charge is treated in the following conditions:
Pressure: 25 bars
Temperature: 80° C.
Charge feed rate in volume per volume of catalyst and per hour: 5 H2 flow rate in moles per mole of hydrocarbons charge: 0.3

The resultant product has the following composition:

|  | % by weight |  |
| --- | --- | --- |
| 1-pentene | 0.1 |  |
| cis and trans 2-pentenes | 2.0 |  |
| 2-methyl-1-butene | 5.3 | } 32.9 |
| 2-methyl-2-butene | 27.6 |  |
| Pentane | 57.9 |  |
| Isopentane | 7.1 |  |

It is observed that the pentenes have not been completely hydrogenated whereas a substantial part of the isopentenes has been converted to isopentane, the isopentenes content decreasing from 40% to 32.9%.

EXAMPLE 2

(according to the invention)

The operating conditions are the same as in example 1. The treated charge has the same composition as in example 1, except that sulfur, as dimethyl sulfide, is used here at a concentration of 6 ppm by weight.

The composition of the obtained product is as follows:

|  | % by weight |  |
| --- | --- | --- |
| 2-methyl-1-butene | 7.2 | } 39.9 |
| 2-methyl-2-butene | 32.7 |  |
| Pentane | 60 |  |
| Isopentane | 0.1 |  |

Here it is observed that all pentenes were hydrogenated, whereas isopentenes were almost entirely unconverted. Moreover, 2-methyl-2-butene has been isomerized, said hydrocarbon being in a proportion corresponding to that determined by the thermodynamic laws (82% of the total amount of isopentenes).

EXAMPLE 3

(according to the invention)

In this example, the catalyst is the same as in examples 1 to 2. The treated charge originates from a catalytic cracking unit and its composition is that given in table 1. This charge further contains 12 ppm by weight of sulfur, as compounds of undetermined structure.

The operating conditions are as follows:

| Pressure | 28 bars |
| --- | --- |
| Temperature | 80° C. |
| Feed rate of the charge by volume per volume of catalyst and per hour | 3 |
| H2 feed rate in mole per mole of charge | 0.3 |

The resultant product has the following composition:

| Hydrocarbons | % by weight |
| --- | --- |
| Isopentane | 39.10 |
| n-pentane | 30.80 |
| Cyclopentane | 2.10 |
| 2-methyl-1-butene | 5.04 |
| 2-methyl-2-butene | 22.96 |

What is claimed as the invention is:

1. A process for producing 2-methyl-2-butene from a charge containing olefins of 5 carbon atoms, including 2-methyl-1-butene and at least one n-pentene, wherein a mixture of said charge with hydrogen is contacted with a supported catalyst comprising at least one noble metal from group VIII, at a temperature from 60°-120° C., and wherein the reactants mixture contains 2-50 ppm by weight, expressed as sulfur, with respect to the hydrocarbon charge,, of at least one sulfur compound and in that the pressure ranges from 5 to 100 bars.

2. A process according to claim 1, wherein palladium is the noble metal of the catalyst and is used in a proportion from 0.01 to 2% by weight of the catalyst.

3. A process according to claim 1, wherein the pressure is from 25 to 50 bars.

4. A process according to claim 1, wherein the sulfur compound content, expressed as sulfur, ranges from 5 to 30 ppm by weight with respect to the hydrocarbons charge.

5. A process according to claim 2, wherein the catalyst is palladium supported on alumina.

6. A process according to claim 1, wherein the charge comprises 2-methyl-2-butene in a concentration below the thermodynamic equilibrium with 2-methyl-1-butene.

7. A process according to claim 1, wherein the charge is essentially free of 2-methyl-2-butene.

8. A process according to claim 2, wherein the palladium is used in a proportion of from 0.1–0.5% by weight of the catalyst.

9. A process according to claim 1, wherein the feed rate of the $C_5$ cut is 0.5–20 liters per hour per liter of catalyst, and the amount of hydrogen is about 5–90 mole % with respect to the $C_5$ hydrocarbons in the feed.

10. A process according to claim 1, wherein the sulfur compound is a thiol, sulfide, disulfide, thiophene, thiourea, thioaldehyde, thioketone, dithiocarbamate, or thiocyanate.

11. A process according to claim 10, wherein the sulfur compound is hydrogen sulfide, dimethylsulfide, dimethyldisulfide, ethanethiol, thioacetone or butanethiol.

12. A process according to claim 11, wherein the sulfur compound is dimethylsulfide.

13. A process according to claim 1, wherein the temperature is 80° C.

* * * * *